(12) United States Patent
Friske et al.

(10) Patent No.: US 8,672,907 B2
(45) Date of Patent: Mar. 18, 2014

(54) DRAINABLE OSTOMY POUCH

(75) Inventors: Timothy A. Friske, Round Lake Beach, IL (US); Patrick D. Ertel, St. Joseph, MI (US)

(73) Assignee: Hollister Incorporated, Libertyville, IL (US)

( * ) Notice: Subject to any disclaimer, the term of this patent is extended or adjusted under 35 U.S.C. 154(b) by 249 days.

(21) Appl. No.: 12/843,457

(22) Filed: Jul. 26, 2010

(65) Prior Publication Data

US 2012/0022478 A1    Jan. 26, 2012

(51) Int. Cl.
    *A61F 5/44*    (2006.01)
(52) U.S. Cl.
    USPC .......................................................... 604/335
(58) Field of Classification Search
    USPC .......................................................... 604/335
    See application file for complete search history.

(56) References Cited

U.S. PATENT DOCUMENTS

| | | |
|---|---|---|
| 2,520,831 A | 8/1950 | Chincholl |
| 2,782,785 A | 2/1957 | Arcand |
| 3,189,253 A | 6/1965 | Mojonnier |
| 3,251,390 A | 5/1966 | Evans |
| 3,406,853 A | 10/1968 | McLeod |
| 3,408,705 A | 11/1968 | Kayser et al. |
| 3,473,532 A | 10/1969 | Eisenberg |
| 3,507,282 A | 4/1970 | Burding |
| 3,523,534 A | 8/1970 | Nolan |
| 3,567,074 A | 3/1971 | Brown |
| 3,688,973 A | 9/1972 | Salomo Lillkvist |
| 3,690,320 A | 9/1972 | Riely |
| 3,724,461 A | 4/1973 | Eisenberg |
| 3,734,154 A | 5/1973 | Polk |
| 3,825,005 A | 7/1974 | Fenton |
| 3,895,118 A * | 7/1975 | Rambold ........................ 426/83 |
| 3,897,780 A | 8/1975 | Trousil |

(Continued)

FOREIGN PATENT DOCUMENTS

| | | |
|---|---|---|
| DE | 29 36 622 A1 | 3/1981 |
| EP | 1 378 218 A1 | 1/2004 |

(Continued)

OTHER PUBLICATIONS

International Search Report and Written Opinion for Application No. PCT/US2011/038290, dated Aug. 18, 2011.

(Continued)

*Primary Examiner* — Susan Su
*Assistant Examiner* — Guy K Townsend
(74) *Attorney, Agent, or Firm* — Levenfeld Pearlstein, LLC

(57) ABSTRACT

A drainable ostomy pouch is disclosed having generally parallel sidewalls of flexible sheet material joined along their edges to define a chamber therebetween and having a downwardly extending neck portion terminating in a discharge opening for draining the contents from the chamber. The neck portion of the pouch has first and second transversely extending curved spring members associated therewith and is closed by folding the neck portion upwardly. The first curved spring member is located nearer the discharge opening than the second curved spring member and each of the curved spring members is curved smoothly and outwardly relative to the neck portion. The curved spring members are located relative to one another so the first curved spring member nearer the discharge opening nests with the second curved spring member when the neck portion has been folded upwardly and can be secured using a two-part fastening system during use of the drainable ostomy pouch.

18 Claims, 6 Drawing Sheets

(56) References Cited

U.S. PATENT DOCUMENTS

| | | | |
|---|---|---|---|
| 3,924,631 A | 12/1975 | Mancusi, Jr. | |
| 4,050,468 A | 9/1977 | Wynnyk | |
| 4,230,115 A | 10/1980 | Walz, Jr. et al. | |
| 4,233,977 A | 11/1980 | Mattson | |
| 4,310,952 A | 1/1982 | Robben et al. | |
| 4,403,991 A * | 9/1983 | Hill | 604/337 |
| 4,411,659 A | 10/1983 | Jensen et al. | |
| 4,439,191 A | 3/1984 | Hogan | |
| 4,441,659 A | 4/1984 | Marklund | |
| 4,460,359 A | 7/1984 | Fenton | |
| 4,465,486 A | 8/1984 | Hill | |
| 4,519,797 A * | 5/1985 | Hall | 604/332 |
| 4,561,540 A | 12/1985 | Hunter et al. | |
| 4,596,566 A | 6/1986 | Kay | |
| 4,686,814 A | 8/1987 | Yanase et al. | |
| 4,726,956 A * | 2/1988 | Christie | 426/80 |
| 4,755,177 A | 7/1988 | Hill | |
| 4,838,874 A | 6/1989 | Eisenberg | |
| 4,869,725 A | 9/1989 | Schneider et al. | |
| 4,898,477 A | 2/1990 | Cox et al. | |
| 4,983,172 A | 1/1991 | Steer et al. | |
| 4,988,343 A | 1/1991 | Ballan et al. | |
| 5,000,500 A | 3/1991 | Almog et al. | |
| 5,030,211 A | 7/1991 | Zakroczymski | |
| 5,037,138 A | 8/1991 | McClintock et al. | |
| 5,037,149 A | 8/1991 | Beck | |
| 5,044,774 A | 9/1991 | Bullard et al. | |
| 5,132,124 A * | 7/1992 | Tamaki et al. | 426/82 |
| 5,174,658 A | 12/1992 | Cook et al. | |
| 5,184,896 A | 2/1993 | Hammond et al. | |
| 5,457,855 A | 10/1995 | Kenney et al. | |
| 5,545,154 A | 8/1996 | Oberholtzer | |
| D379,654 S | 6/1997 | Holtermann | |
| 5,643,234 A | 7/1997 | Lesko | |
| 5,647,670 A | 7/1997 | Iscovich | |
| 5,690,621 A | 11/1997 | Canela | |
| 5,745,926 A | 5/1998 | Cailleteau | |
| 5,842,408 A * | 12/1998 | Hatta | 99/323 |
| 5,941,640 A | 8/1999 | Thatcher | |
| 5,968,023 A | 10/1999 | Olsen | |
| 5,968,024 A | 10/1999 | Freeman | |
| 6,212,716 B1 | 4/2001 | Logan, Jr. et al. | |
| 6,267,506 B1 | 7/2001 | Campion | |
| 6,336,918 B1 | 1/2002 | Olsen et al. | |
| 6,419,664 B1 | 7/2002 | von Bulow et al. | |
| 6,544,241 B2 | 4/2003 | Morton | |
| 6,589,221 B1 | 7/2003 | Olsen et al. | |
| 6,644,854 B2 | 11/2003 | Lien | |
| 6,726,667 B2 | 4/2004 | Leise, Jr. et al. | |
| 6,780,172 B2 | 8/2004 | Olsen et al. | |
| 6,858,023 B2 | 2/2005 | Poulsen | |
| 6,887,222 B2 | 5/2005 | Mandzij et al. | |
| 7,223,260 B2 | 5/2007 | Hansen et al. | |
| 7,306,581 B2 | 12/2007 | Falconer et al. | |
| 7,468,056 B2 | 12/2008 | Burt | |
| 7,722,585 B2 | 5/2010 | Falconer et al. | |
| D618,791 S | 6/2010 | Schena | |
| 7,947,025 B2 * | 5/2011 | Buglino et al. | 604/335 |
| 2001/0037627 A1 | 11/2001 | Hausslein | |
| 2002/0010444 A1 | 1/2002 | Wiltshire et al. | |
| 2002/0111659 A1 | 8/2002 | Davis et al. | |
| 2002/0165507 A1 | 11/2002 | Hessel et al. | |
| 2003/0028160 A1 | 2/2003 | Leise et al. | |
| 2003/0073962 A1 | 4/2003 | Olsen et al. | |
| 2003/0153882 A1 * | 8/2003 | Mandzij et al. | 604/334 |
| 2003/0167042 A1 | 9/2003 | Poulsen | |
| 2004/0049837 A1 | 3/2004 | Falconer et al. | |
| 2004/0068243 A1 * | 4/2004 | Hansen et al. | 604/327 |
| 2004/0171999 A1 * | 9/2004 | Andersen et al. | 604/332 |
| 2005/0131360 A1 | 6/2005 | Villefrance et al. | |
| 2005/0159717 A1 | 7/2005 | Holtermann | |
| 2005/0283126 A1 | 12/2005 | Schena et al. | |
| 2006/0015079 A1 | 1/2006 | Mandzij et al. | |
| 2006/0111682 A1 | 5/2006 | Schena et al. | |
| 2007/0265588 A1 | 11/2007 | Pedersen | |
| 2008/0033379 A1 | 2/2008 | Pedersen | |
| 2008/0051743 A1 * | 2/2008 | Falconer et al. | 604/332 |
| 2008/0097360 A1 | 4/2008 | Andersen et al. | |
| 2008/0226864 A1 | 9/2008 | Willis et al. | |
| 2008/0269699 A1 | 10/2008 | O'Toole | |
| 2008/0269700 A1 | 10/2008 | O'Toole et al. | |
| 2009/0043271 A1 | 2/2009 | Winther | |
| 2009/0082743 A1 | 3/2009 | Buglino et al. | |
| 2009/0143755 A1 | 6/2009 | Schertiger | |
| 2009/0192479 A1 | 7/2009 | Schertiger | |
| 2009/0234312 A1 | 9/2009 | O'Toole et al. | |
| 2009/0247971 A1 | 10/2009 | Schena et al. | |
| 2010/0174254 A1 * | 7/2010 | Tsai | 604/332 |
| 2011/0028923 A1 * | 2/2011 | Murray | 604/332 |
| 2011/0144601 A1 * | 6/2011 | Villefrance et al. | 604/340 |
| 2012/0022477 A1 * | 1/2012 | Grum-Schwensen | 604/332 |

FOREIGN PATENT DOCUMENTS

| | | |
|---|---|---|
| FR | 2 870 112 A1 | 11/2005 |
| GB | 2 000 683 A | 1/1979 |
| GB | 2 268 065 A | 1/1994 |
| GB | 2 346 328 A | 8/2000 |
| GB | 2 398 743 A | 9/2004 |
| GB | 2 414 677 A | 12/2005 |
| JP | 59-28052 U | 2/1984 |
| JP | 09-301386 A | 11/1997 |
| JP | 2006043037 | 8/2004 |
| WO | WO-96/19164 A1 | 6/1996 |
| WO | WO-99/25278 A1 | 5/1999 |
| WO | WO-99/66859 A2 | 12/1999 |
| WO | WO-01/28470 A1 | 4/2001 |
| WO | WO-01/51383 A1 | 7/2001 |
| WO | WO-03/065944 A1 | 8/2003 |
| WO | WO-2008/134334 A1 | 11/2008 |
| WO | WO-2010/077377 A1 | 7/2010 |

OTHER PUBLICATIONS

International Search Report for Application No. PCT/US2002/034773, dated Feb. 26, 2003.

* cited by examiner

176° Typical Bend

DRAINABLE OSTOMY POUCH

FIELD OF THE DISCLOSURE

The present disclosure generally relates to drainable ostomy pouches and, more particularly, to drainable ostomy pouches having integral and secure closure systems.

BACKGROUND OF THE DISCLOSURE

Drainable ostomy pouches are well known as shown, for example, in Nolan U.S. Pat. No. 3,523,534 and Jensen et al. U.S. Pat. No. 4,441,659, and such a pouch typically has flat opposing sidewalls secured together along their edges and defining a chamber for receiving body waste material. One of the walls is provided with a stoma-receiving opening, and means are provided for securing the pouch to a patient's abdomen so that waste discharged from the stoma is received in the chamber. At its lower end, the drainable pouch has a discharge opening for draining waste material, usually provided at the end of a narrowed neck portion. Closure means is provided for maintaining the discharge opening in sealed condition until waste material is to be drained from the pouch, and the closure means may take the form of a clamp, as in the aforementioned Nolan patent, or a device such as conventional wire ties or wraps for securing the neck portion in an upwardly-rolled condition.

A drainable ostomy pouch is reusable following periodic emptying of body waste material, but it is well recognized that effective cleaning is necessary prior to reuse so that effective resealing can be assured and odors emanating from the resealed pouch can be avoided. Users often encounter difficulty and discomfort in unsealing, emptying, cleaning and resealing drainable pouches because of the direct exposure to waste matter and because the manipulations may require greater dexterity than a patient, particularly an elderly patient, can provide. Adding to the problem is the fact that residual amounts of solid and/or liquid waste matter at the lower end of a drainable ostomy pouch tend to block or hold the walls of the pouch together, making cleaning of the inside surfaces adjacent the discharge opening even more difficult.

SUMMARY OF THE DISCLOSURE

The drainable ostomy pouch of the disclosure has generally parallel sidewalls of flexible sheet material joined along their edges to define a chamber therebetween including a downwardly extending neck portion terminating in a discharge opening for draining the contents from the chamber. The neck portion of the pouch has first and second transversely extending curved spring members associated therewith and is closed by folding the neck portion upwardly. The first curved spring member is located nearer the discharge opening than the second curved spring member and each of the spring members is curved smoothly and outwardly relative to the neck portion. The curved spring members are located relative to one another so the first curved spring member nearer the discharge opening nests with the second curved spring member when the neck portion has been folded upwardly.

In an exemplary embodiment, the first curved spring member is at or near the discharge opening and has first and second transversely extending edges. The first transversely extending edge is thus located at or near the discharge opening with the second transversely extending edge being disposed generally parallel to the first transversely extending edge. In this embodiment, the second curved spring member can be longitudinally adjacent the second transversely extending edge of the first curved spring member.

Specifically, the neck portion can have a pair of opposite sides and each of the first and second curved spring members can be associated with the neck portion in opposed fashion with one on each of the two sides. As a result of having first and second curved spring members on opposite sides of the neck portion, the first curved spring member can nest with the second curved spring member after the neck portion has been folded upwardly a single time.

In another embodiment, the first curved spring member is again at or near the discharge opening and has first and second transversely extending edges. The first transversely extending edge is therefore, again, preferably located at or near the discharge opening with the second transversely extending edge being disposed generally parallel to the first transversely extending edge. In this embodiment, the second curved spring member is spaced longitudinally from the second transversely extending edge of the first curved spring member.

Specifically, the neck portion again can have a pair of opposite sides but in this embodiment both of the first and second curved spring members associated with the neck portion are on the same one of the opposite sides. As a result of having the first and second curved spring members on the same one of the sides, the first curved spring member can nest with the second curved spring member after the neck portion has been folded upwardly two times.

In both embodiments, the drainable ostomy pouch advantageously includes a two-part fastening system comprising first and second fastener strips. The fastener strips are preferably associated with the flexible sheet material at different distances from the discharge opening and have fastener elements for releasable interlocking engagement with one another. Thus, the fastener strips can secure a curved coil comprised of the smoothly and outwardly curved and nested first and second curved spring members.

In particular, the fastener strips may be releasably interlockingly engaged with one another after the neck portion has been folded upwardly a sufficient number of times to cause the first curved spring member to nest with the second curved spring member.

With this arrangement, the neck portion again can have a pair of opposite sides and each of the first and second fastener strips can therefore be associated with a different one of the opposite sides of the neck portion. In addition, the one of the first and second fastener strips located furthest from the discharge opening is preferably associated with a fastener flap for securing the curved coil after the neck portion has been folded upwardly.

Other advantages and features of the disclosure will become apparent from the following specification when considered in view of the accompanying drawings.

DETAILED DESCRIPTION OF THE DISCLOSURE

Figure 1B:
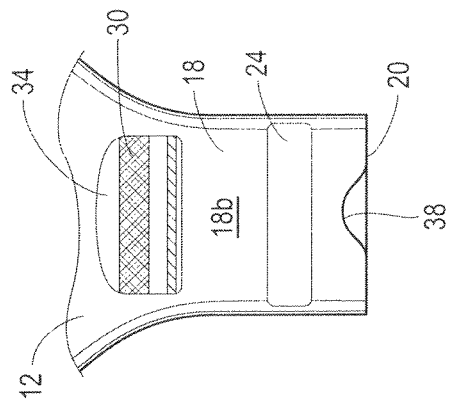
FIG. 1B is a view similar to FIG. 1A without a second spring member on the non-body side but with a thumb notch cutout on the non-body side adjacent the discharge opening.
Figure 1A:
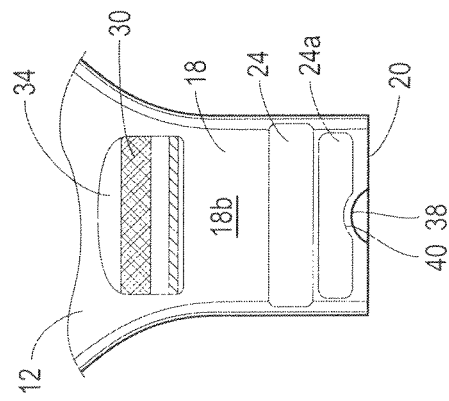
FIG. 1A is a view similar to FIG. 1 illustrating a second spring member on the non-body side and a thumb notch cutout on the non-body side adjacent the discharge opening.
Figure 1:
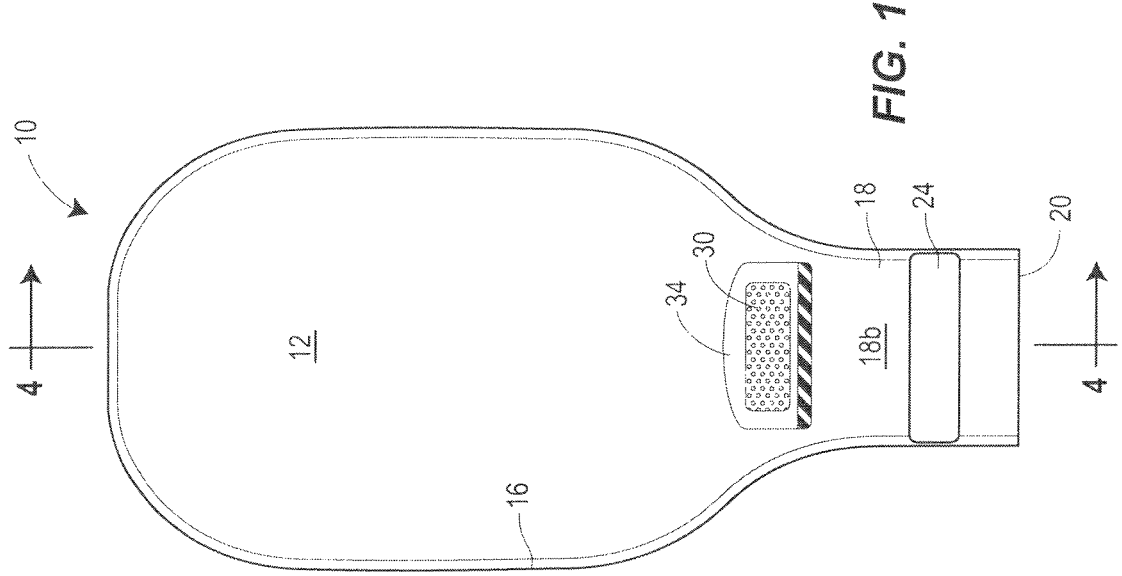
FIG. 1 is a front elevational view illustrating the non-body side of a drainable ostomy pouch having a curved spring member on the neck portion.
Figure 2:
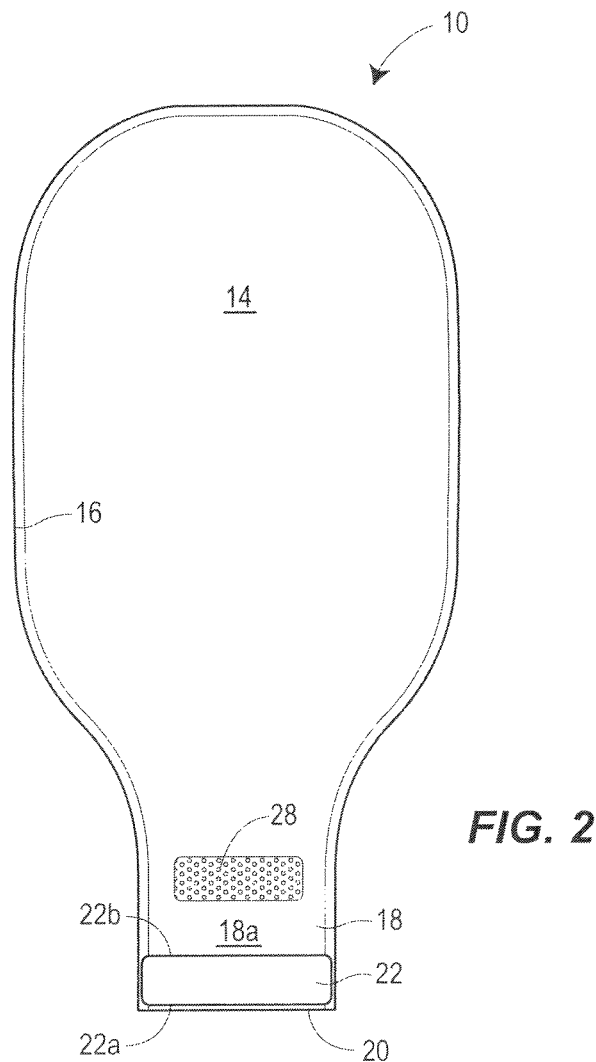
FIG. 2 is a rear elevational view illustrating the body side of a drainable ostomy pouch having a curved spring member on the neck portion.
Figure 3:
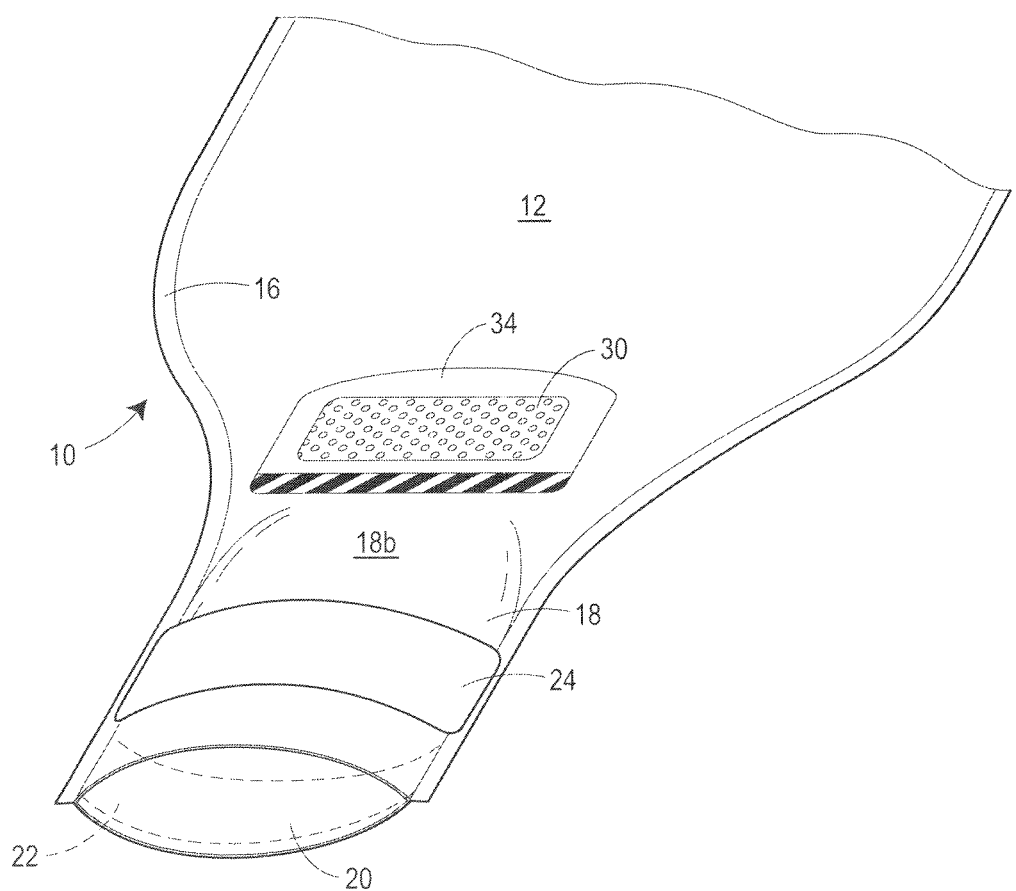
FIG. 3 is a perspective view illustrating the non-body side of the drainable ostomy pouch of FIG. 1 before folding the neck portion upwardly.

With reference first to FIGS. 1 and 2, the drainable ostomy pouch 10 has generally parallel sidewalls 12 and 14 joined along their edges as at 16 to define a chamber therebetween. The drainable ostomy pouch 10 also has a downwardly extending neck portion 18 terminating in a discharge opening 20 for draining the contents from the chamber after a period of use. The discharge opening 20 of the drainable ostomy pouch 10 is closed during use by folding the neck portion 18 upwardly and securing it in the upwardly folded position. The neck portion 18 has first and second transversely extending curved spring members 22 and 24 with the first curved spring member 22 located nearer the discharge opening 20 than the second curved spring member 24. As best shown in FIG. 3, the first and second curved spring members 22 and 24 are each formed such that they are curved smoothly and outwardly relative to the neck portion 18.

By utilizing spring members 22 and 24 that are curved smoothly and outwardly relative to the neck portion 18, they can be located relative to one another so the first curved spring member 22 nearer the discharge opening 20 nests with the second curved spring member 24 when the neck portion 18 has been folded upwardly. The nesting relationship of the smoothly and outwardly curved first and second spring members 22 and 24 is illustrated in FIG. 5. In the embodiment of the drainable ostomy pouch 10 illustrated in FIGS. 1-5, it will be appreciated that the first curved spring member 22 is located relative to the second curved spring member 24 such that they achieve a curved nesting relationship (see FIG. 5) after the neck portion 18 has been folded upwardly a single time.

Figure 4:
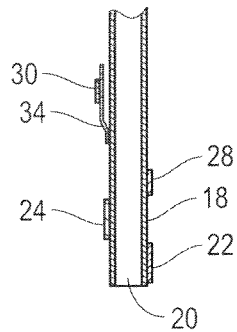
FIG. 4 is a longitudinal cross-sectional view of the drainable ostomy pouch of FIG. 1 taken along the line 4-4.
Figure 5:
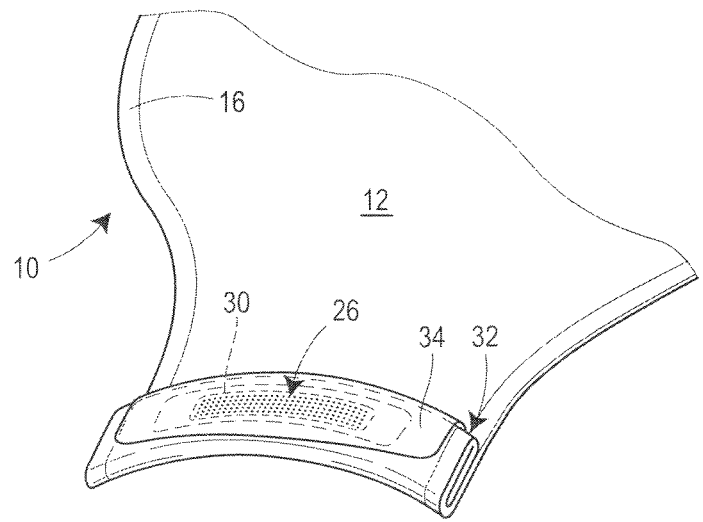
FIG. 5 is a perspective view of the drainable ostomy pouch of FIG. 1 after folding the neck portion upwardly and engaging the fastening system.

Referring to FIG. 4, the first curved spring member 22 is preferably located at or near the discharge opening 20. The first curved spring member 22 has first and second transversely extending edges 22a and 22b (see, also, FIG. 2) and, as illustrated in FIGS. 2 and 4, the first edge 22a is located generally at or near the discharge opening 20 whereas the second edge 22b is generally parallel to the first edge 22a. The second curved spring member 24 is located longitudinally adjacent the second edge 22b of the first curved spring member 22.

As will be appreciated, the neck portion 18 has a pair of opposite sides 18a and 18b and each of the first and second curved spring members 22 and 24 are associated with a different one of the pair of opposite sides. With the smoothly and outwardly curved first and second curved spring members 22 and 24 located as in FIGS. 1-4, they can nest with one another after a single upward fold of the neck portion 18, as previously described.

Referring to FIGS. 1, 2, 4 and 5, the drainable ostomy pouch 10 also includes a two-part fastening system 26 comprising first and second fastener strips 28 and 30 which are associated with the flexible sheet material comprising the generally parallel sidewalls 12 and 14. As illustrated in the drawings, the first and second fastener strips 28 and 30 are located at different distances from the discharge opening 20, and they have fastener elements which are adapted for releasable interlocking engagement. The fastener elements associated with the first and second fastener strips 28 and 30 can be engaged to secure a curved coil 32 (FIG. 5) comprised of the smoothly and outwardly curved first and second curved spring members 22 and 24 after folding the neck portion 18 upwardly.

As previously mentioned, the neck portion 18 has a pair of opposite sides 18a and 18b and each of the first and second fastener strips 28 and 30 is associated with a respective one of the opposite sides 18a and 18b. Referring to FIG. 1, the one of the first and second fastener strips 28 and 30 located furthest from the discharge opening 20, i.e., the fastener strip 30 on the side 18b, is associated with a fastener flap 34 for securing the curved coil 32.

In one embodiment, the first and second fastener strips 28 and 30 may comprise a polypropylene material of the type sold under the trademark DUOTEC by G. Binder GmbH & Co. Holzgerlingen, Germany which is stated in product literature to work on the principle of interlocking mushroom elements. By using strips of this synthetic material for the first and second fastener strips 28 and 30, the discharge opening 20 can be maintained in closed position (FIG. 5) absent a disengagement force sufficient to overcome the retention force. Further, the interlocking mushroom elements are designed so both strips can be identical and, thus, there is no need to use physically distinguishable male/female components, or to use any fabric-like material that will have a strong tendency to absorb body waste materials and odors and then be difficult to clean.

Among the attributes for this material is its ability to provide a solid connection when pressed firmly together, its characteristic locking action that provides a user with a tactile indication of when the fastener strips are interlocked, and its ability to be repeatedly reopened and closed. The opening and closing action of fastener strips formed of this material also produces only very limited noise. However, it is to be understood that other types of fastening means may be used which lack at least some of the attributes and advantages described above such as, for example, hook and loop fasteners as marketed under the Velcro trademark or pressure sensitive adhesive coatings.

Referring to FIG. 4, the first and second curved spring members 22 and 24 are longitudinally offset, i.e., the first curved spring member 22 is located nearer the discharge opening 20 than the second curved spring member 24. As previously described, the first curved spring member 22 is located at or near the discharge opening 20 and, in the illustrated embodiment, it will be appreciated that the curved spring member 22 is located closely adjacent the discharge opening 20. Referring to FIG. 3, it will also be appreciated that the first and second transversely extending spring members 22 and 24 are each preferably curved smoothly and outwardly to be concave in relation to the neck portion 18.

Referring to FIG. 1A, the neck portion 18 has been provided with an additional curved spring member 24a between the curved spring member 24 and the discharge opening 20 on the side 18b opposite the first curved spring member 22. It will also be noted that a thumb notch cutout 38 has been formed in the thin ostomy film of the sidewall 12 at the discharge opening 20 on the side 18b opposite the first curved spring member 22. In addition, the additional curved spring member 24a has a small thumb notch cutout 40 which generally conforms in shape to the cutout 38, and both cutouts 38 and 40 are generally disposed along the longitudinal axis of the ostomy pouch 10.

With this arrangement, it is possible for the user to insert a thumb or finger in the region of the thumb notch cut out 38 to facilitate separation of the thin ostomy films forming the sidewalls 12 and 14 at the discharge opening 20 in the event they should have any tendency to stick together as a result of any liquid or semi-solid body waste material between them despite the biasing effect of the curved spring members 22, 24 and 24a.

Referring to FIG. 1B, it closely corresponds to FIG. 1A, except the neck portion 18 has not been provided with an additional curved spring member between the curved spring member 24 and the discharge opening 20. Instead, this embodiment has an enlarged thumb notch cut out 38 in the thin ostomy film forming the sidewall 12, and it extends across approximately one third the width of the discharge opening 20. While this embodiment does not include an additional curved spring member, the enlarged thumb notch cut out 38 more readily facilitates inserting a thumb or finger to assist in separating the thin ostomy films at the discharge opening 20.

Referring to FIGS. 6, 7, 8A and 8B, the neck portion 18' of an alternative embodiment of drainable ostomy pouch is illustrated. The only difference between the drainable ostomy pouch 10 illustrated in FIGS. 1-5 and this alternative embodiment is in the neck portion 18' so the entire pouch has not been illustrated. In both embodiments, the respective drainable ostomy pouches can take the form of any conventional ostomy pouch.

Figure 6:
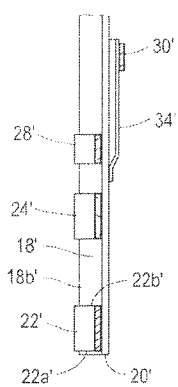
FIG. 6 is a perspective view illustrating the curved spring members on the same side of the neck portion in an alternative embodiment.
Figure 7:
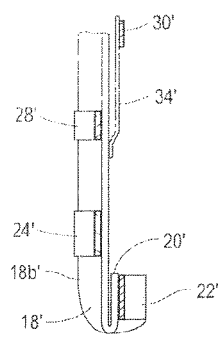
FIG. 7 is a perspective view of the alternative embodiment of FIG. 6 after the neck portion has been folded upwardly a single time.

As shown in FIG. 6, the first and second curved spring members 22' and 24' are longitudinally offset so the first curved spring member 22' is located nearer the discharge opening 20' than the second curved spring member 24'. It will be seen that the first curved spring member 22' is preferably located in relatively close proximity to the discharge opening 20' and, preferably, at or near so as to be closely adjacent the discharge opening 20'. As also shown in FIG. 6, the first and second transversely extending spring members 22' and 24' are each preferably curved smoothly and outwardly to be concave in relation to the neck portion 18'.

As will be appreciated, the neck portion 18' has a pair of opposite sides including non-body side 18b' and each of the first and second curved spring members 22' and 24' is associated with the same one of the pair of opposite sides, i.e., the non-body side 18b' in FIGS. 6, 7, 8A and 8B. Unlike first and second curved spring members 22 and 24 in FIGS. 1-5, the second curved spring member 24' is not located longitudinally adjacent the second transversely extending edge 22b' of the first curved spring member 22'. Rather than being disposed in longitudinally adjacent relation, FIG. 6 illustrates the second curved spring member 24' being located in longitudinally spaced relation to the second transversely extending edge 22b' of the first curved spring member 22'.

Preferably, the respective transverse and longitudinal dimensions of the two sets of first and second curved spring members 22, 24 and 22', 24' are all substantially the same. This facilitates being able to place the curved spring members into a congruent nesting relationship after the respective neck portions 18, 18' have been folded upwardly. As previously mentioned in the discussion of the embodiment of FIGS. 1-5, the curved spring members 22 and 24 nest after the neck portion 18 has been folded upwardly a single time.

With the embodiment which is illustrated in FIGS. 6, 7, 8A and 8B, the curved spring members 22', 24' are preferably longitudinally spaced apart by a distance which is approximately the same as their respective longitudinal dimensions. With this longitudinal spacing, the first curved spring member 22' adjacent the discharge opening 20' will nest with the second curved spring member 24' after the neck portion 18' has been folded upwardly two times (see FIGS. 7 and 8A).

While the embodiment in FIGS. 1-5 has been illustrated for nesting of the first and second curved spring members 22 and 24 following a single upward fold of the neck portion 18, and the embodiment in FIGS. 6, 7, 8A and 8B has been illustrated for nesting of the first and second curved spring members 22' and 24' following two upward folds of the neck portion 18', it will be appreciated that this could be varied.

Specifically, with the first and second transversely extending curved spring members 22 and 24 on opposite sides 18a and 18b of the neck portion 18, the curved spring members 22 and 24 can suitably be located for nesting following an odd number of folds, i.e., 1, 3, etc. Similarly, with the first and second curved spring members 22' and 24' in longitudinally spaced relation on the same side 18a' of the neck portion 18', the curved spring members 22' and 24' can suitably be located for nesting following an even number of folds, i.e., 2, 4, etc.

Figure 8A:
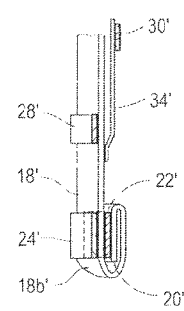
FIG. 8A is a perspective view of the alternative embodiment of FIG. 6 after the neck portion has been folded upwardly two times.
Figure 8B:
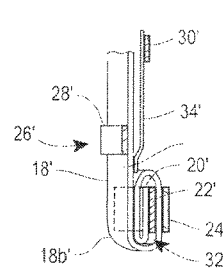
FIG. 8B is a perspective view of the alternative embodiment of FIG. 6 after the neck portion has been folded upwardly three times.
Figure 8C:
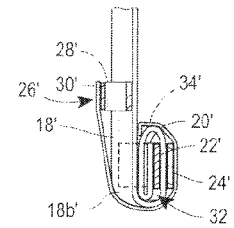
FIG. 8C is a perspective view similar to FIG. 8B illustrating the flap folded to the other side of the neck portion and secured in a closed position.

As with the embodiment of FIGS. 1-5, the alternative embodiment of drainable ostomy pouch illustrated in FIGS. 6, 7, 8A and 8B can also include a two-part fastening system 26' (see FIG. 8B). The two-part fastening system 26' comprises first and second fastener strips 28' and 30' associated with the flexible sheet material comprising the generally parallel sidewalls at different distances from the discharge opening 20' when positioned as shown in FIG. 6. The fastener strips 28' and 30' have fastener elements for releasable interlocking engagement to secure a curved coil 32' comprised of the first and second curved spring members 22' and 24' after the neck portion 18' has been folded upwardly two times to cause the curved spring members 22' and 24' to nest and a third time to ensure against leakage (see FIGS. 8A-8C). In this connection, each of the first and second fastener strips 28' and 30' is associated with a different one of the pair of opposite sides of the neck portion 18', with one of the fastener strips 30' preferably being associated with a fastener flap 34'. In this connection, it will be appreciated that the fastener flap 34' has been cut away along the longitudinal centerline in FIGS. 6, 7 and 8A-8C to understand the folds and nesting of strips 22' and 24'.

Like the embodiment of FIGS. 1-5, it is the fastener strip 30' located furthest from the discharge opening 20' as shown in FIG. 6 that is associated with a fastener flap 34' for securing the curved coil 32'.

Figure 9A:
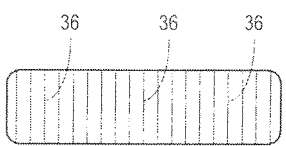
FIG. 9A is a top plan view of a curved spring member for a drainable ostomy pouch in accordance with the disclosure.
Figure 9B:
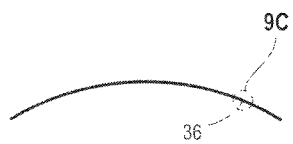
FIG. 9B is a front elevational view illustrating the curvature of the curved spring member illustrated in FIG. 9A.
Figure 9C:
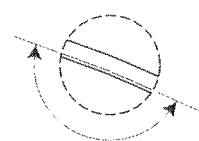
FIG. 9C is a diagrammatic view illustrating a typical bend in each of the multiple bend locations illustrated in FIG. 9A.

Referring to FIGS. 9A-9C, details of the first and second transversely extending curved spring members for both embodiments can be understood. The curved spring members 22, 22' and 24, 24' may be formed by thermal forming, extruding, or molding using a suitable polymer material such as, for example, MYLAR® brand PET available from DuPont and may be on the order of approximately 0.25 mm in thickness. With regard to the transverse dimension, it should be chosen to substantially cover the entire width of the neck portion.

The longitudinal dimension of the curved spring members will typically comprise approximately one quarter the transverse dimension although this can be varied depending upon the various parameters for other components including the width and length of the neck portion.

Referring to FIG. 9A, the curved spring members 22, 22' and 24, 24' preferably have a plurality of longitudinally extending bends 36. The bends 36 can be evenly spaced across the transverse dimension of the curved spring members, and they are preferably spaced apart on the order of approximately 3.5 mm. In addition, each of the bends 36 may be formed at an angle of approximately 176° in order to achieve the desired curvature curvature (FIG. 9C).

More specifically, one manner of obtaining the desired curvature for the curved spring members 22, 22' and 24, 24' is illustrated in FIG. 9B where the curvature is formed by providing a plurality of typical bends 36 of approximately 176° as illustrated in FIG. 9C. By forming the curved spring members with such bends 36, and adhesively attaching them to the neck portion 18 or 18' in longitudinally spaced relation, the curved spring members will have a natural ability to open the discharge opening 20, 20'. When the fastener strips of the two-part fastening system are disengaged and the neck portion 18, 18' folded downward, the discharge opening 20, 20' is opened by the curved spring members 22, 22' and 24, 24'.

As a result, the curved spring members are normally able to overcome any tendency of the flexible sheet material of the opposite sides of the neck portion to adhere to one another. This facilitates an ostomate's ability to drain the contents from the chamber of the drainable ostomy pouch as well as to clean immediately inside the discharge opening by forming a natural hinge type "coin purse" opening. After cleaning, the neck portion can again be folded up to seat or nest the curved spring members to provide a more secure system than straight members or directly opposed concave members.

By utilizing curved spring members on the neck portion of a drainable ostomy pouch generally near the discharge opening, either with the curved spring members in opposed longitudinally offset fashion (see curved spring members 22 and 24 in FIGS. 1-5) or with the curved spring members in "same way facing" longitudinally offset fashion (see curved spring members 22' and 24' in FIGS. 6, 7, 8A and 8B), the curved spring members can always remain in their curved condition, even during use of the drainable ostomy pouch.

Unlike directly opposed concave members, the curved spring members 22, 22' and 24, 24' are still curved even when the neck portion has been folded upwardly and the fastener strips have been interlockingly engaged. Thus, instead of the curved spring members 22, 22' and 24, 24' being forced against one another and then retained in a flattened closed "use" position to create a seal while acting against the retainer as they attempt to return to their curved condition, the curved spring members are disposed in a curved nesting relationship in the closed "use" position. Further, the use of the curved spring members 22, 22' and 24, 24' results in moving the fastener strips of the two-part fastening system further away from the discharge opening where they are less likely to become soiled.

Additional advantages of the present disclosure include the bi-stable effect achieved on the last fold when placing the components in a position ready for use, and the curvature of the nested curved spring members secured by the two-part fastening system conforming to the user's leg when the drainable ostomy pouch is being used.

While in the foregoing there has been provided a detailed description of the disclosure, it will be appreciated that the details herein given may be varied by those skilled in the art without departing from the true scope and spirit of the appended claims.

What is claimed is:

1. A drainable ostomy pouch having generally parallel sidewalls of flexible sheet material joined along their edges to define a chamber therebetween and having a downwardly extending neck portion terminating in a discharge opening for draining the contents from the chamber, the discharge opening being closed by folding the neck portion upwardly, the neck portion having first and second transversely extending curved spring members associated therewith, the first curved spring member being located nearer the discharge opening than the second curved spring member and each of the spring members being curved smoothly and outwardly relative to the neck portion, the curved spring members being located relative to one another so the first curved spring member nearer the discharge opening nests with the second curved spring member when the neck portion has been folded upwardly, wherein the first curved spring member and the second curved spring member remain in a curved nesting relationship to form a curved coil, wherein the first curved spring member has first and second lateral edges and the second curved spring member has first and second lateral edges, wherein the first lateral edge of the first curved spring member is laterally aligned with the first lateral edge of the second curved spring member, and the second lateral edge of the first curved spring member is laterally aligned with the second lateral edge of the second curved spring member, wherein the first curved spring member is at or near the discharge opening, the first curved spring member having first and second transversely extending edges with the first transversely extending edge being at or near the discharge opening and the second transversely extending edge generally parallel to the first transversely extending edge, the second curved spring member being longitudinally adjacent the second transversely extending edge of the first curved spring member, wherein the neck portion has a pair of opposite sides and each of the first and second curved spring members is associated with a different one of the pair of opposite sides.

2. The drainable ostomy pouch of claim 1 wherein the first curved spring member adjacent the discharge opening nests with the second curved spring member after the neck portion has been folded upwardly a single time.

3. A drainable ostomy pouch having generally parallel sidewalls of flexible sheet material joined along their edges to define a chamber therebetween and having a downwardly extending neck portion terminating in a discharge opening for draining the contents from the chamber, the discharge opening being closed by folding the neck portion upwardly, the neck portion having first and second transversely extending curved spring members associated therewith, the first curved spring member being located nearer the discharge opening than the second curved spring member and each of the spring members being curved smoothly and outwardly relative to the neck portion, the curved spring members being located relative to one another so the first curved spring member nearer the discharge opening nests with the second curved spring member when the neck portion has been folded upwardly, wherein the first curved spring member and the second curved spring member remain in a curved nesting relationship to form a curved coil, wherein the first curved spring member has first and second lateral edges and the second curved spring member has first and second lateral edges, wherein the first lateral edge of the first curved spring member is laterally aligned with the first lateral edge of the second curved spring member, and the second lateral edge of the first curved spring member is laterally aligned with the second lateral edge of the second curved spring member, wherein the first curved spring member is located at or near the discharge opening, the first curved spring member having first and second transversely extending edges with the first transversely extending edge being located at or near the discharge opening and the second transversely extending edge generally parallel to the first transversely extending edge, the second curved spring member being longitudinally spaced from the second transversely extending edge of the first curved spring member, wherein the neck portion has a pair of opposite sides and each of the first and second curved spring members is associated with the same one of the pair of opposite sides.

4. The drainable ostomy pouch of claim 3 wherein the first curved spring member adjacent the discharge opening nests with the second curved spring member after the neck portion has been folded upwardly two times.

5. The drainable ostomy pouch of claim 1 including a two-part fastening system comprising first and second fastener strips associated with the flexible sheet material at different distances from the discharge opening and having fastener elements for releasable interlocking engagement to secure a curved coil comprised of the smoothly and outwardly curved first and second curved spring members after the neck portion has been folded upwardly to cause the first curved spring member to nest with the second curved spring member.

6. The drainable ostomy pouch of claim 5 wherein the neck portion has a pair of opposite sides and each of the first and second fastener strips is associated with a different one of the pair of opposite sides.

7. The drainable ostomy pouch of claim 6 wherein one of the first and second fastener strips located furthest from the discharge opening is associated with a fastener flap for securing the curved coil.

8. The drainable ostomy pouch of claim 6 wherein one of the first and second fastener strips located nearest to the discharge opening is associated with a fastener flap for securing the curved coil.

9. The drainable ostomy pouch of claim 1 including a thumb notch cutout in the downwardly extending neck portion at the discharge opening in the sidewall opposite the first curved spring member.

10. The drainable ostomy pouch of claim 9 including an additional curved spring member between the second curved spring member and the discharge opening adjacent the thumb notch cutout.

11. The drainable ostomy pouch of claim 10 wherein the additional curved spring member has a thumb notch cutout generally conforming to the thumb notch cutout in the sidewall at the discharge opening.

12. The drainable ostomy pouch of claim 3 including a two-part fastening system comprising first and second fastener strips associated with the flexible sheet material at different distances from the discharge opening and having fastener elements for releasable interlocking engagement to secure a curved coil comprised of the smoothly and outwardly curved first and second curved spring members after the neck portion has been folded upwardly to cause the first curved spring member to nest with the second curved spring member.

13. The drainable ostomy pouch of claim 12, wherein the neck portion has a pair of opposite sides and each of the first and second fastener strips is associated with a different one of the pair of opposite sides.

14. The drainable ostomy pouch of claim 13 wherein one of the first and second fastener strips located furthest from the discharge opening is associated with a fastener flap for securing the curved coil.

15. The drainable ostomy pouch of claim 13 wherein one of the first and second fastener strips located nearest to the discharge opening is associated with a fastener flap for securing the curved coil.

16. The drainable ostomy pouch of claim 3 including a thumb notch cutout in the downwardly extending neck portion at the discharge opening in the sidewall opposite the first curved spring member.

17. The drainable ostomy pouch of claim 16 including an additional curved spring member between the second curved spring member and the discharge opening adjacent the thumb notch cutout.

18. The drainable ostomy pouch of claim 17 wherein the additional curved spring member has a thumb notch cutout generally conforming to the thumb notch cutout in the sidewall at the discharge opening.

* * * * *